United States Patent
Schmettow

[11] Patent Number: 6,031,893
[45] Date of Patent: Feb. 29, 2000

[54] STRAY RADIATION GRID

[75] Inventor: Dieter Schmettow, Erlangen, Germany

[73] Assignee: Siemens Aktiengesellschaft, Munich, Germany

[21] Appl. No.: 09/098,426

[22] Filed: Jun. 17, 1998

[30] Foreign Application Priority Data

Jun. 24, 1997 [DE] Germany .............. 197 26 846

[51] Int. Cl.[7] ............................................ G21K 1/00

[52] U.S. Cl. ............................................ 378/154; 378/149

[58] Field of Search .................... 378/145, 147, 378/149, 154

[56] References Cited

U.S. PATENT DOCUMENTS

| | | |
|---|---|---|
| 4,951,305 | 8/1990 | Moore et al. . |
| 5,231,655 | 7/1993 | Wei et al. .............................. 378/147 |
| 5,303,282 | 4/1994 | Kwasnick et al. ..................... 378/147 |
| 5,606,589 | 2/1997 | Pelligrino et al. ..................... 378/154 |

Primary Examiner—David P. Porta
Attorney, Agent, or Firm—Hill & Simpson

[57] ABSTRACT

A stray radiation grid, particularly for a medical X-ray apparatus, is composed of a carrier material with absorption elements, particularly in the form of lead lamellae, that are arranged in rows spaced from one another and proceeding essentially parallel to one another, with the respective spacings between the successive rows of absorption elements being larger in the region of the edges of the grid than in the middle region.

19 Claims, 2 Drawing Sheets

| f | 750 | 900 | 1200 | 1500 | 1800 |
|---|---|---|---|---|---|
| k | 420 | 420 | 420 | 420 | 420 |
| α | 15.6422 | 13.1340 | 9.9262 | 7.9696 | 6.6544 |
| r | 15 | 15 | 15 | 15 | 15 |
| F | 5.24 | 4.53 | 3.64 | 3.11 | 2.76 |

| f | 750 | 900 | 1200 | 1500 | 1800 |
|---|---|---|---|---|---|
| k | 420 | 420 | 420 | 420 | 420 |
| α | 15.6422 | 13.1340 | 9.9262 | 7.9696 | 6.6544 |
| r | 12 | 12 | 12 | 12 | 12 |
| F | 4.40 | 3.83 | 3.12 | 2.69 | 2.41 |

| f | 750 | 900 | 1200 | 1500 | 1800 |
|---|---|---|---|---|---|
| k | 420 | 420 | 420 | 420 | 420 |
| α | 15.6422 | 13.1340 | 9.9262 | 7.9696 | 6.6544 |
| r | 10 | 10 | 10 | 10 | 10 |
| F | 3.84 | 3.36 | 2.77 | 2.41 | 2.17 |

| f | 750 | 900 | 1200 | 1500 | 1800 |
|---|---|---|---|---|---|
| k | 420 | 420 | 420 | 420 | 420 |
| α | 15.6422 | 13.1340 | 9.9262 | 7.9696 | 6.6544 |
| r | 8 | 8 | 8 | 8 | 8 |
| F | 3.28 | 2.89 | 2.42 | 2.13 | 1.94 |

STRAY RADIATION GRID

BACKGROUND OF THE INVENTION

1. Field of the Invention

The present invention is directed to a stray radiation grid, particularly for a medical X-ray apparatus of the type composed of a carrier material with absorption elements, particularly in the form of lead lamellae, that are arranged in rows spaced from one another and proceeding essentially parallel to one another, whereby the spacing between the rows of absorption elements is larger in the region of the edges of the grid than in the middle region.

2. Description of the Prior Art

Stray radiation grids are employed in X-ray diagnostics for the suppression of stray radiation. The effectiveness of such a grid is particularly characterized by the line density (in lines per centimeter) and by its geometry, i.e. the ratio of height and thickness of the intermediate medium. This ratio is called the shaft ratio. In order to avoid a higher occlusion by the absorption elements, i.e., for example, the lead lamellae, in the outside regions than in the center, the grids are fashioned such that the absorption elements are aligned to the focus of the radiator, i.e. are "focussed". The focus spacing is thus a characteristic quantity of such grids. In these known grids, thus, the lead lamellae are arranged tilted. Alternatively, it is also known to conically erode the finished grid at one side, proceeding from the middle, and thus to modify the geometry. The known grids are composed of a carrier usually composed of paper; the absorption elements are usually lead lamellae. A disadvantage of the known embodiments is, for the first version described above, the manufacture thereof, since the lead lamellae arranged focussed, i.e. residing obliquely, must be brought into this focussing alignment in a complicated and extremely precise way. In the case of the slanted grid, the post-processing during manufacture is extremely involved.

A stray radiation grid of the above-described type is described in U.S. Pat. No. 4,951,305. Given this grid, the spacing of the absorption elements of the respective grid or plane varies such that it is smaller in the middle of the grid than at the edge regions. A disadvantage, however, is that the grid exhibits a different absorption behavior over its area or surface caused by the increasing spacing of the absorption elements.

SUMMARY OF THE INVENTION

An object of the present invention is to provide a stray radiation grid with optimally uniform absorption behavior.

This object is inventively achieved in a stray radiation grid of the type initially described, but wherein the width of the absorption elements is larger (thicker) in the region of the edges of the grid than in the middle.

The grid thus departs from the extremely complicated tilting of the absorption elements, or beveling thereof, both of these techniques maintaining same spacing of the absorption elements. On the contrary, the absorption elements in the inventive stray radiation grid are seated closer to one another in the middle region than in the outer edge region, so that the shaft ratio is approximately balanced as a result, due to the oblique incidence of the image-active beam. A shaft ratio that is virtually constant over the entire grid is expediently achieved when the spacing from row to row increases continuously toward the edge proceeding from the middle of the grid. Since the absorption behavior changes with increasing spacing of the absorption elements from one another, it is inventively provided for compensation that the width of the absorption elements is larger in the region of the edges of the grid than in the middle, with the per element width increasing continuously toward the edges proceeding from the middle. On the basis of this measure, it is possible to realize a largely uniform absorption behavior over the entire grid width. The respective widths are thereby inventively selected such that they increase essentially proportionally to the increasing row spacing, i.e. such that the lead content per length unit remains constant over the entire grid width.

In a further embodiment of the inventive grid, by contrast, the width increases sub-proportionately to the increasing row spacing. This inventive embodiment makes it possible to take the imaging radiation and the stray radiation which decrease toward the edge of an extensive grid (due to the distance square law), into consideration, so that a largely uniform absorption behavior is also established in the critical edge regions. Moreover, this embodiment allows the grid to be adapted to the decreasing dose rate in the beam cone, which decreases toward the edges. It is especially expedient, given an absorption property adapted to the actual conditions and given a constant setting of the shaft ratio, when the respective spacings between the absorption elements and/or the width of the absorption elements are inventively selected dependent on the local incident angle of the radiation, particularly X-ray radiation, in order to achieve a complete focussing with reference to the spacing from the radiation source.

Compared to the continuous increase in spacing, in an alternative embodiment of the invention the grid, proceeding from the middle, has a number of regions within which the spacings between the rows of absorption elements are respectively constant, but the row spacing increases from region to region proceeding from the middle. This stray radiation grid is thus inventively constructed of separate segments that are respectively constant in terms of spacing; the spacing, however, the spacing increases from segment to segment. A precise focussing given substantial constancy of the shaft ratio can also be achieved with this inventive embodiment. Given this grid constructed of segments, the absorption elements are also thicker in the edge region than in middle. The width of the absorption elements can be essentially constant within a region, but can increase from region to region proceeding from the middle, as is also the case in the first embodiment of the invention. Here, too, there is the possibility for the width to increase essentially proportionately to the increasing spacing or, particularly given extensive grids, the width can increase subproportionately to the increasing spacing in order to adapt to the imaging radiation and the stray radiation decreasing at the edge side. Here, too, the spacing and/or width within the regions can be selected dependent on the incident angle of the radiation, particularly X-ray radiation, for a further improvement of the focussing.

DESCRIPTION OF THE PREFERRED EMBODIMENTS

Figures 1, 2:
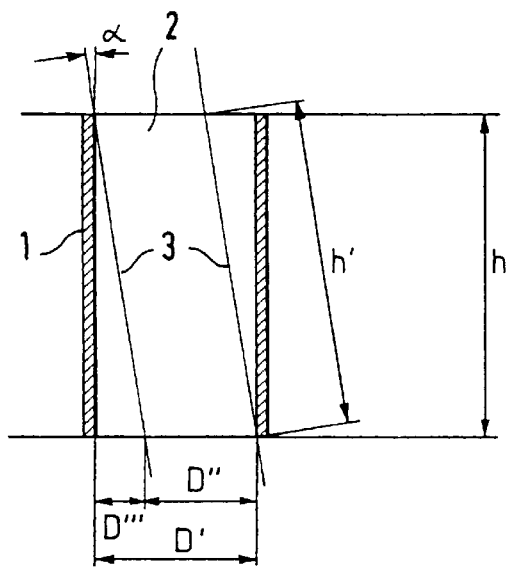
FIG. 1 is a sectional view of a portion of stray radiation grid for explaining the inventive principle.
FIG. 2 is a table for various grids with different shaft ratios, respectively calculated for different foci.

FIG. 1 shows a portion of a stray radiation grid that is composed of lead lamellae 1 and the carrier medium 2, here in the form of a paper layer. Two incident X-rays 3 are also shown in the schematic drawing. The computational description of the inventive stray radiation grid is recited below with reference to FIG. 1. The grid is constructed of parallel lead lamellae 1 having the characteristic quantities:

d=thickness of the lead lamellae

D=thickness of the carrier medium along the center line of the grid h=height of the lead lamellae f=focussing spacing.

The shaft ratio r is calculated as follows along the center lie, i.e. in the middle of the grid:

$$r=h/d.$$

Due to the oblique incidence of the X-rays (angle a relative to the center ray) of the image-producing rays and given the same height h of the lead lamellae 1, the same shaft ratio is achieved toward the grid edge when the spacing of the lead lamellae 1 is correspondingly enlarged. The following then applies according to FIG. 1:

$$h=r \cdot D;$$

$$h=h/\cos \alpha;$$

$$D=D/\cos \alpha;$$

$$D=h \cdot \tan \alpha.$$

The lamella spacing D' dependent on the incident angle of the radiation then is derived as follows:

$$D'=D''+D'''$$

$$=D/\cos \alpha + H \cdot \tan \alpha$$

$$=D/\cos \alpha + r \cdot D \cdot \tan \alpha$$

$$=D \cdot (1/\cos \alpha + r \cdot \tan \alpha).$$

With $F=(1/\cos \alpha + r \cdot \tan \alpha)$, then $D'=D \cdot F$.

F is a factor dependent on the incident angle that increases with increasing distance from the middle toward the edge and exhibits its maximum value at the edge.

Accordingly, d'~D' and, thus, $$d'=d \cdot (1/\cos \alpha + r \cdot \tan \alpha) = d \cdot F$$

applies for a constant lead content per length unit.

In the practical embodiment, however, the lead content of the grid will be advantageously sub-proportionally increased relative to the lamella spacing because the imaging radiation and the stray radiation decrease toward the edge (given extensive grids) as a result of the distance square law. The focussing of stray radiation grids with adapted line or element density additionally allows the grid to be adapted to the decreasing dose rate in the ray cone toward the outside.

In the form of a table for different grid-focus spacings given a constant grid width k, i.e. the side length perpendicular to the lead lamellae 1, and a constant shaft ratio, FIG. 2 shows the different F-values arising therefrom, with the maximum F-value occurring at the grid edge being outlined. In addition, the table indicates the respective a-values at the extreme edge of the grid with which the calculation was implemented as an example; f and k are respectively indicated in millimeters, α in degrees, r and F have no dimension. As can be seen, the F-value decreases with increasing focus distance, due to the smaller and smaller incident angle. The same decrease also occurs with decreasing shaft ratio, i.e. the F-value also decreases here as the shaft ratio becomes smaller and smaller.

Figure 3:
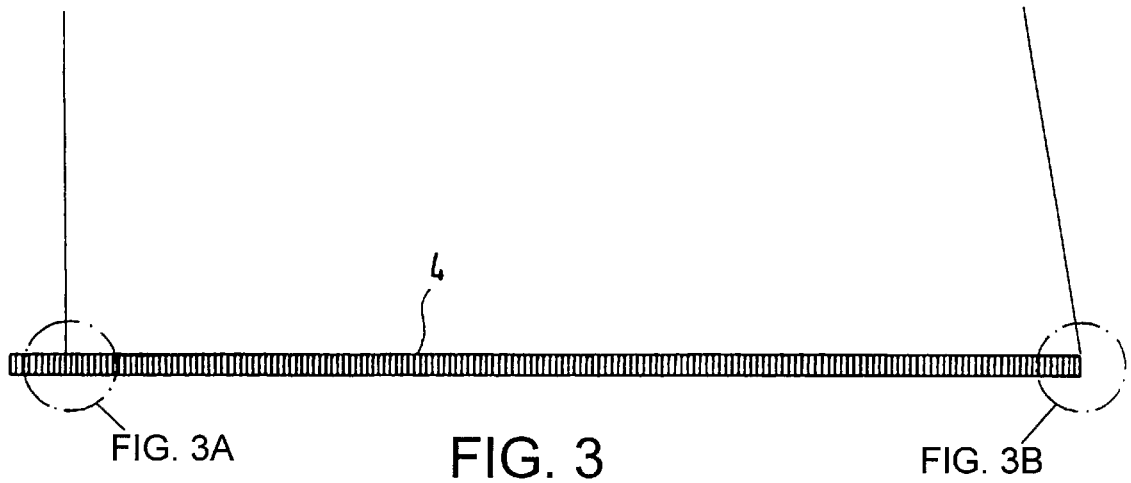
FIG. 3 is a partial section of an inventive stray radiation grid.
Figure 3A:
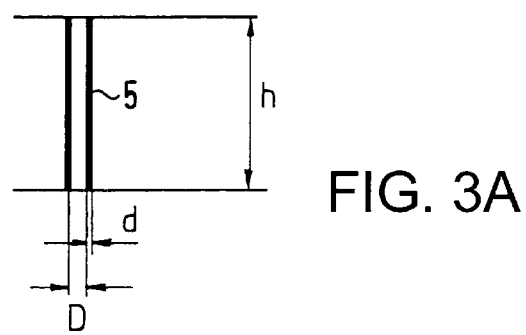
FIG. 3A shows an enlarged detail of a middle section through the stray radiation grid of FIG. 3.
Figure 3B:
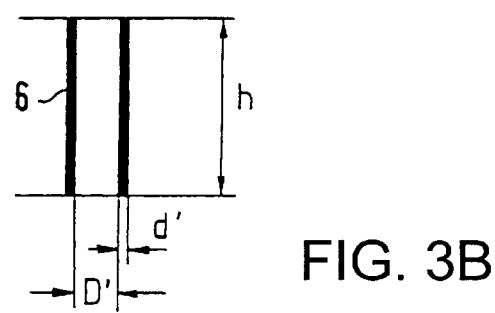
FIG. 3B is an enlarged detail of a section through an edge region of the stray radiation grid of FIG. 3.

FIG. 3 shows an exemplary embodiment of the invention wherein, in addition to an enlargement of the lamella spacing itself, the thickness of the lamellae also increases from the middle toward the edge. A section through a stray radiation grid 4 is shown in FIG. 3. Respective regions of interest in the middle of the grid (FIG. 3A) and at the edge of the grid (FIG. 3B) are shown enlarged. As can be seen, the spacing D of the lamellae in the region of the middle of the grid is clearly smaller than the spacing D' of the lamellae 6 at the edge of the grid, as is computationally derived from the above equation. In order to have a constant lead content per length unit, the lamella thickness is likewise increases toward the edge, proceeding from the middle, which, as the above equations indicate, can also be computationally determined. This means that the value d is smaller than the value d'. The following spacing and thickness values in the middle of the grid or at the edge of the grid, respectively, derive for the stray radiation grid having the parameters indicated dot-dashed in FIG. 2:

| Grid middle: | Grid edge: |
|---|---|
| D = 40 μm | D' = d · 2.69 = 107.6 μm |
| d = 8 μm | d' = d · 2.64 = 21.52 μm |

The invention is not limited to the illustrated exemplary embodiments of stray radiation grids composed of lead lamellae 1 and paper as carrier medium. The invention can likewise be applied to the recently developed silicon stray radiation grids, whereby the respective spacing increase and thickening of absorption elements can be unproblemmatically achieved using photolithographic means, so that corresponding stray radiation grids optimized in view of the focussing can also be easily produced for different focus distances.

According to an alternative embodiment of the invention, the grid shown in FIG. 3 can be composed of a number of segments arranged next to one another with the lamella spacing and lamella thickness being constant with a segment, but changing from segment to segment. For each segment, the spacing therein is selected as the average of the edge values calculated at its edge, the same being true of the lamella thickness.

The invention is not limited to the illustrated embodiments but can also be applied given different types of stray radiation grids having a different structure or composed of different materials.

Although various minor modifications might be suggested by those skilled in the art, it should be understood that my wish to embody within the scope of the patent warranted hereon all such modifications as reasonably and properly come with the scope of my contribution to the art.

I claim as my invention:

1. A stray radiation grid comprising:

a carrier;

a plurality of lamellae disposed on said carrier forming radiation absorption elements, said lamellae being disposed in a plurality of rows in a grid, with said rows being spaced from each other and proceeding substantially parallel to each other, each of said lamellae having a width and said grid having a middle region and edge regions;

said rows being spaced from each other at a spacing at said edge regions of said grid which is larger than a spacing of said rows from each other in said middle region of said grid; and the width of lamellae disposed in said edge regions of said grid being larger than the width of lamellae disposed in said middle of said grid.

2. A stray radiation grid as claimed in claim 1 wherein a spacing of said rows of lamellae increases continuously from row to row proceeding from the middle region of the grid to the edge regions of said grid.

3. A stray radiation grid as claimed in claim 2 wherein each of said lamellae has a width continuously increasing from said middle region of said grid toward said edge regions of said grid.

4. A stray radiation grid as claimed in claim 3 wherein said width increases substantially proportionally relative to an increase in spacing between said rows.

5. A stray radiation grid as claimed in claim 3 wherein said width increases sub-proportionally relative to an increasing spacing between said rows.

6. A stray radiation grid as claimed in claim 3 wherein said stray radiation grid is subjected to incident radiation striking said stray radiation grid at a plurality of incident angles, each of said lamellae having a local incident angle, among said plurality of incident angles, respectively associated therewith, and wherein the spacing between neighboring rows increases from said middle region of said grid to said edge regions of said grid dependent on the respective local incident angles of said radiation.

7. A stray radiation grid as claimed in claim 3 wherein said stray radiation grid is subjected to incident radiation striking said stray radiation grid at a plurality of incident angles, each of said lamellae having a local incident angle, among said plurality of incident angles, respectively associated therewith, and wherein the width of each of said lamellae rows increases from said middle region of said grid to said edge regions of said grid dependent on the respective local incident angles of said radiation.

8. A stray radiation grid as claimed in claim 3 wherein said stray radiation grid is subjected to incident radiation striking said stray radiation grid at a plurality of incident angles, each of said lamellae having a local incident angle, among said plurality of incident angles, respectively associated therewith, and wherein the spacing between neighboring rows and the width of each of said lamellae increase from said middle region of said grid to said edge regions of said grid dependent on the respective local incident angles of said radiation.

9. A stray radiation grid as claimed in claim 1 wherein each of said lamellae has a width continuously increasing from said middle region of said grid toward said edge regions of said grid.

10. A stray radiation grid as claimed in claim 9 wherein said width increases substantially proportionally relative to an increase in spacing between said rows.

11. A stray radiation grid as claimed in claim 9 wherein said width increases sub-proportionally relative to an increasing spacing between said rows.

12. A stray radiation grid as claimed in claim 9 wherein said stray radiation grid is subjected to incident radiation striking said stray radiation grid at a plurality of incident angles, each of said lamellae having a local incident angle, among said plurality of incident angles, respectively associated therewith, and wherein the width of each of said lamellae rows increases from said middle region of said grid to said edge regions of said grid dependent on the respective local incident angles of said radiation.

13. A stray radiation grid as claimed in claim 1 wherein said grid comprises a plurality of grid regions proceeding from said middle region of said grid to said edge regions of said grid, each of said grid regions having a spacing of the rows therein which is constant within that grid region, and the respective spacings of the rows in the respective grid regions increasing from grid region to grid region proceeding from said middle region of said grid to said edge regions of said grid.

14. A stray radiation grid as claimed in claim 13 wherein the width of said lamellae is substantially constant within each of said grid regions, and the respective widths of the lamellae in respective regions increasing from region to region, proceeding from said middle region of said grid to said edge regions of said grid.

15. A stray radiation grid as claimed in claim 8 wherein said width increases substantially proportionally relative to the increase in said spacing from grid region to grid region.

16. A stray radiation grid as claimed in claim 8 wherein said width increases substantially sub-proportionally relative to the increase in said spacing from grid region to grid region.

17. A stray radiation grid as claimed in claim 14 wherein said stray radiation grid is subjected to incident radiation which is incident on said stray radiation grid at a plurality of local incident angles, each of said grid regions having one of said local incident angles respectively associated therewith, and wherein the spacing between said rows in each grid region is dependent on the local incident angle respectively associated with that grid region.

18. A stray radiation grid as claimed in claim 14 wherein said stray radiation grid is subjected to incident radiation which is incident on said stray radiation grid at a plurality of local incident angles, each of said grid regions having one of said local incident angles respectively associated therewith, and wherein the width of each of said lamellae in each grid region is dependent on the local incident angle respectively associated with that grid region.

19. A stray radiation grid as claimed in claim 14 wherein said stray radiation grid is subjected to incident radiation which is incident on said stray radiation grid at a plurality of local incident angles, each of said grid regions having one of said local incident angles respectively associated therewith, and wherein the spacing between said rows and the width of each of said lamellae in each grid region is dependent on the local incident angle respectively associated with that grid region.

* * * * *